United States Patent [19]

Warunek et al.

[11] Patent Number: 5,112,640
[45] Date of Patent: May 12, 1992

[54] SILICONE ELASTOMER LINED PROSTHETIC DEVICES AND METHODS OF MANUFACTURE

[75] Inventors: Stephen P. Warunek, Lancaster; Soren E. Sorensen, Williamsville, both of N.Y.

[73] Assignee: The Research Foundation of State University of New York University at Buffalo, Buffalo, N.Y.

[21] Appl. No.: 519,165

[22] Filed: May 4, 1990

[51] Int. Cl.$^5$ .............................................. A01N 1/02
[52] U.S. Cl. ...................................... 427/2; 427/322; 427/327; 427/387; 433/168.1; 433/171
[58] Field of Search ................. 433/168.1, 171; 427/2, 427/322, 327, 387; 156/307.5

[56] References Cited

U.S. PATENT DOCUMENTS

| 3,445,420 | 5/1969 | Kookootsedes et al. | 260/37 |
| 3,637,416 | 1/1972 | Misch et al. | 433/168.1 |
| 3,785,054 | 1/1974 | Van Handel | 433/168.1 |
| 4,623,593 | 11/1986 | Baier et al. | 428/447 |
| 4,677,139 | 6/1987 | Feinmann et al. | 523/111 |

OTHER PUBLICATIONS

Dow-Corning, New Product Information, Silastic ® Q7-4720 Medical GrADE ETR Elastomer.
W. T. Bell et al, J. of Prosthetic Dentistry, vol. 54, No. 3, Sep., 1985, pp. 404-410.
S. Parker et al. J. of Dentistry, vol. 10, No. 2, 1982, pp. 149-153.
P. S. Wright, J. of Dental Research, vol. 61, No. 8, 1982, pp. 1002-1005.
Eastman Plastics, Injection Molding Kodar ® PETG Copolyester 6763, Jan., 1986.
A. Udagama, J. of Prosthetic Dentistry, vol. 48, No. 1, Jul., 1982, pp. 86-88.
R. G. Craig, Restorative Dental Materials, C. V. Mosely Co. 1989, pp. 542-544 and 547-549.
J. F. Wolfaardt, J. of Prosthetic Dentistry, vol. 53, No. 2, Feb. 1985, pp. 228-234.
R. E. Ogle et al., J. of Prosthetic Dentistry, vol. 56, No. 4, Oct., 1986, pp. 497-506.
M. T. Singer, J. of Prosthetic Dentistry, vol. 60, No. 5, Nov., 1988, pp. 602-605.

*Primary Examiner*—Michael Lusignan
*Attorney, Agent, or Firm*—Hodgson, Russ, Andrews, Woods & Goodyear

[57] ABSTRACT

Organopolysiloxane elastomers comprising copolymers of dimethyl and methylvinyl siloxanes provide improved facial and dental prosthetic materials, and are especially useful in preventing and treating chronic tissue irritation due to hard dental polymers. They are effectively bonded to polymeric and metallic substrates as denture liners, obturators, maxillofacial prosthetic devices and appliances with a group of trifunctional silane coupling agents.

12 Claims, No Drawings

SILICONE ELASTOMER LINED PROSTHETIC DEVICES AND METHODS OF MANUFACTURE

BACKGROUND OF THE INVENTION

This invention relates generally to prosthetic devices and methods of manufacture, and more specifically, to maxillofacial prosthetic devices and dental appliances having permanent silicone elastomers bonded thereto forming composite structures with enhanced strength, dimensional stability and elasticity.

Prosthodontic devices, such as dentures typically consist of a baseplate of a hard resin, such as poly(methyl methacrylate) which supports the artificial teeth for chewing, and also enhances esthetics. Difficulty can arise, however, due to the inability of patients to tolerate the hard baseplate. As a result, there is need for a resilient liner which may be affixed to the denture base to cushion soft tissues of the oral cavity. Ideally, such materials should be permanently resilient, inert, cleanable, substantially water insoluble, have low watersorption properties and good tensile and tear strength. While softness is desirable for comfort, the liner must also be sufficiently firm to displace soft tissues of the mouth and permit grinding of the denture periphery to avoid creating sore spots. From a practical view point, the dental appliance should also be capable of fabrication under conditions generally found in dental laboratories, avoiding extremes in temperature and pressure, or the need for special equipment.

Laboratory and clinical studies have shown that few, if any, of the present materials used as resilient liners and prosthetic devices, for example, are satisfactory in all respects. Most common shortcomings include inadequate strength and elasticity, high rate of water diffusion through the elastomer and subsequent staining and deterioration. Frequently, with the discovery of a potentially improved prosthodontic material having what might appear to be fewer of such shortcomings, the material is compromised due to the inability to satisfactorily bond the elastomer to dental base plastics and other prosthetic appliances.

Accordingly, there is a need for improved facial and dental prosthetic elastomeric materials possessing properties of strength, elasticity, dimensional stability, low water sorption and toxicity, including methods which enable convenient bonding to most dental base polymers with a high degree of permanence and reliability. Such materials and methods would be useful in fabricating prosthodontic devices, such as dentures with improved elastomeric liners for preventing and treating chronic tissue irritation from hard dental polymers and for cushioning soft tissues; liners after oral surgery, maxillofacial prosthetic devices, like obturators for defects in the palate, and the like.

SUMMARY OF THE INVENTION

Accordingly, it is a principal object of the invention to provide a method of forming a composite-like structure of a silicone elastomer, generally referred to as an organopolysiloxane, and a prosthetic appliance by the steps of:

a) applying a film of a coupling agent to the appliance, the coupling agent comprising a compound of the formula:

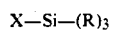

$$X-Si-(R)_3 \quad (I)$$

wherein X is methyl or vinyl and R is $-O-CO-CH_3$ or $-O-N=C-(CH_3)-CH_2CH_3$;

b) drying the silane film on the appliance;

c) applying to the dried silane film on said appliance a silicone elastomer to form the composite-like structure, the elastomer comprising a copolymer of dimethyl and methylvinyl siloxanes, the elastomer when in the form of about a 0.075 inch thick slab, press cured for about 10 minutes at about 230° to about 250° F. and cured for about 24 hours at about 21° to about 25° C. and at a relative humidity of about 45 to about 55 percent is characterized by a specific gravity ranging from about 1.08 to about 1.12 as determined by ASTM D 792; a Shore A durometer in a range from about 19 to about 27 as determined by ASTM D 2240; a tensile strength of at least 1100 psi as determined by ASTM D 412, Die C; an elongation of at least 1050 percent as determined by ASTM D 412, Die C; a tear strength of at least 140 ppi as determined by ASTM D 624, Die B, and d) curing the composite structure at above ambient temperature conditions.

Prosthetic appliance as mentioned herein is intended to mean principally prosthodontic devices, such as dentures, obturators, splints, etc. However, the present invention also contemplates polymeric and steel based, e.g. stainless steel, prosthetic devices for other portions of the anatomy requiring a highly durable, nontoxic resilient material therefor. Thus, the expressions composite/composite-like as used herein is intended to include such representative example as dentures having resilient liners of the silicone elastomer firmly bonded to the base for protecting oral tissues.

It is yet a further object of the present invention to provide for a maxillofacial prosthetic device, e.g. obturator, comprising a resilient, dimensionally stable silicone elastomer comprising a copolymer of dimethyl and methylvinyl siloxanes. The elastomer when in the form of about a 0.075 inch slab, press cured for about 10 minutes at about 230° to about 250° F. and cured for about 24 hours at about 21° to about 25° C. and at a relative humidity of about 45 to about 55 percent is characterized by a specific gravity ranging from about 1.08 to about 1.12 as determined by ASTM D 792; a Shore A durometer in the range from about 19 to about 27 as determined by ASTM D 2240; a tensile strength of at least 100 psi as determined by ASTM D 412, Die C; an elongation of at least 1050 percent as determined by ASTM D 412, Die C, and a tear strength of at least 140 ppi as determined by ASTM D 624, Die B.

A still further object includes oral post surgical devices having bonded thereto resilient, tear resistant, low water sorption, dimensionally stable silicone elastomers comprising the dimethyl and methylvinyl siloxanes. The elastomer when in the form of about a 0.075 inch thick slab, press cured for about 10 minutes at about 230° to about 250° F. and cured for about 24 hours at about 21° to about 25° C. and at a relative humidity of about 45 to about 55 percent is characterized by a specific gravity ranging from about 1.08 to about 1.12 as determined by ASTM D 792; a Shore A durometer in the range from about 19 to about 27 as determined by ASTM D 2240; a tensile strength of at least 1100 psi as determined by ASTM D 412, Die C; an elongation of at least 1050 percent as determined by ASTM D 412, Die C; a tear strength of a least 140 ppi as determined by ASTM 624, Die B.

DETAILED DESCRIPTION OF THE INVENTION

The composite structures of the invention are based on the discovery that a particular grade of organopolysiloxane elastomer, described in greater detail below, possesses unique properties making it adaptable to a wide range of medical and dental prosthetic applications, with particular emphasis on the fields of prosthodontics and maxillofacial prosthetics, including liners for dentures, interim prosthesis, transitional prosthesis, splints, speech aid devices and obturators. As maxillofacial materials the organopolysiloxane elastomers may be used to correct facial defects resulting from surgery, accidents, or even congenital deformities. Noses, ears and eye orbits, or other parts of the head and neck may be replaced by protheses fabricated from these materials, allowing patients to lead a more normal life. It should be understood, however, that the invention is not limited to dental and facial applications, but also contemplates prosthetic applications for other parts of the body whenever the need exists for a resilient, but dimensionally stable, inert medical grade elastomeric material.

The organopolysiloxane elastomers have been found to be especially useful in conjunction with prosthodontic appliances, such as permanent soft lining materials used to replace the fitting surface of a hard plastic denture, either because the patient cannot tolerate a hard fitting surface, or to improve retention of the denture. Other representative applications include maxillofacial devices, such as obturators typically fabricated from a dental base resin and a resilient lining which locks above the margin of the cleft, thus providing retention of the appliance. Other representative composite applications may include Duyzings' plates fabricated from a hard acrylic resin and soft lining inserts.

The organopolysiloxane elastomer coatings and liners are characterized by high elongation, softness, but with dimensional stability and enhanced resistance to tearing, along with low water absorption. The elastomers and their method of preparation are described in detail in U.S. Pat. No. 3,445,420 which is incorporated-by-reference herein. The generally preferred organopolysiloxanes are those copolymers of dimethyl and methylvinyl siloxanes having from about 99.90 to about 99.99 mole percent dimethyl siloxane units and from about 0.01 to about 0.10 mole percent methylvinyl siloxane units. They are also commercially available through ordinary channels of commerce from Dow Corning, Midland, Mich., under the registered trademark, Silastic, and includes such grades of silicone elastomers having the manufacturer's designation Q7-4720. They are supplied by the manufacturer as a two-component kit having separate pouches designated parts A and B. The contents of each can be blended together manually to form the desired elastomer without requiring special equipment, such as a roll mill. Pouches A and B contain the siloxane polymer and the reinforcing filler, fumed silica. The platinum based curing catalysts for increasing molecular weight, which are added to part A only without the elastomer curing, are also disclosed in U.S. Pat. No. 3,445,420. Part B also includes an organoacetylenic curing inhibitor, preferably an acetylenic alcohol, together with a crosslinking agent.

The most preferred Silastic brand elastomer is that designated Q7-4720 which is a copolymer comprising dimethyl and methylvinyl siloxanes in which approximately 99.95 to about 99.97 mole percent is dimethyl siloxane and approximately 0.03 to about 0.05 mole percent is methylvinyl siloxane. When parts A and B are blended together and formed into a slab of about 0.075 inch thickness, press cured for about 10 minutes at about 230° to about 250° F. and cured for about 24 hours at about 21° to about 25° C. and at a relative humidity of approximately 45 to about 55 percent Silastic Q7-4720 can be characterized by a specific gravity ranging from about 1.08 to about 1.12 as determined by ASTM D 792; a Shore A Durometer of about 19 to about 27 as determined by ASTM D 2240; a tensile strength of at least 1100 psi as determined by ASTM D 412, Die C; an elongation of at least 1050 percent as determined by ASTM D 412, Die C, and a tear strength of at least 140 ppi as determined by ASTM D 624, Die B.

While manufacturer's literature on the above elastomers refers to them as—medical grade ETR (enhanced tear resistant) elastomers—, such literature provides no specific teaching or suggestion the elastomers can be used in forming composite-like structures, such as permanent lining materials for prosthodontic appliances, e.g. dentures, without delaminating or separating from the denture base. Silastic brand silicone elastomer grade Q7-4720, according to manufacturer's literature, is suggested in fabricating devices for the health care industry where high elongation and softness are important, such as in balloons, encapsulating and in extrusions. In addition, such literature offers no solution to the problem of how to form strong, reliable bonds in fabricating composite structures with hard plastics, like the acrylics, for example. U.S. Pat. No. 3,445,420 suggests the organopolysiloxanes as coating compositions for metal, wood and glass, but also fails to suggest, or provide other enablement how the elastomers can be laminated to hard polymer substrates to provide strong, reliable bonds therewith.

Accordingly, this invention not only relates to the discovery of a new use in the field of prosthetics for a specific group of organopolysiloxane elastomers, but also contemplates novel methods for reliably bonding them to hard substrates, e.g. prosthetic devices to form composite-like structures, without which the elastomers could not be readily employed. This aspect of the invention is especially significant since prior methods and materials successfully employed in bonding silicone elastomers to a substrate have not been found to be a reliable basis for predicting bonding performance with other elastomers. That is, coupling agents and know-how successfully employed in bonding other grades of dental/medical elastomers to form composite structures have not proven useful in forming satisfactory laminated structures with the silicone elastomers disclosed herein.

Hence, the present invention also contemplates the discovery of a particular group of silane coupling agents and protocols for bonding the foregoing organopolysiloxane elastomers to prosthetic devices. The silane coupling agents found useful in forming permanent bonds with the particular silicone elastomers of the invention to prosthetic devices fall within Formula (I) above. Specific representative examples of especially useful silane coupling agents are methyltriacetoxysilane, vinyltriacetoxysilane, methyltris(methylethylketoximine)silane and vinyltris(methylethylketoximine)silane. The foregoing silanes are known compounds, and are commercially available through ordinary channels of commerce from Petrarch Systems, Bristol, Pa., under catalogue designations M8980, V4800, M9220 and V5050, respectively.

The initial step of forming the composite structure provides for applying the liquid coupling agent to the surface of the dental appliance or other medical device as is, or as a more economic dilute solution, e.g. 25 percent by volume in a suitable solvent, such as methyl methacrylate monomer. For bonds of optimum strength, more than a single coat is preferred. In addition, each coating is preferably dried before applying the next coat, and so on. Most preferably, the silane painted substrate is oven dried above ambient temperature conditions after the final coating of coupling agent has been applied.

Suitable substrates for the composite-like structures comprise materials commonly used in fabricating prosthodontic appliances, such as acrylics, polyesters, polyurethanes and other resinous materials, as well as certain metals, like stainless steel, aluminum, cobalt and chrome. Some of the most widely used hard materials in dentistry are the denture base resins which can also be used in forming the composites. They include the acrylics, such as poly(methyl methacrylate) (PMMA), rubber modified acrylics, vinyl acrylic copolymers, hydrophilic acrylics, fluid acrylics, and so on. Other useful denture base materials are the glycol-modified poly(ethylene terephthalates) which are available under the trademark Kodar PETG copolyester 6763, a clear amorphous polymer available from Eastman Chemical Products, Inc., Kingsport, Tenn.; and urethane polymers, such as a visible light curable urethane dimethacrylate polymers available under the trademark Triad from Dentsply International, Inc., York, Pa.

Frequently, dental polymers like PMMA contain polymerization initiators, such as ABIN or benzoyl peroxide. The presence of such initiators in the polymeric material may contaminate the platinum catalyst system of the silicone elastomer, and consequently, the elastomer may not fully cure. For this reason it is preferred that the hard polymeric substrates of the composite structure be in a precured condition, substantially free of such initiators.

The resilient silicone elastomer previously described can then be prepared and applied to the silane coated denture base or other prosthetic device to provide an appropriate liner, protective coating, etc. Because Silastic grade Q7-4720 will cure at room temperature as well as at elevated temperatures, Parts A and B of the two part material are manually blended at this stage and applied to the dried silane coated surface employing techniques which assure intimate contact between the uncured elastomer and silane coated substrate. Such methods are generally known by persons of ordinary skill. The coated/lined prosthetic appliance is then cured at elevated temperatures to form the composite, generally in the range of approximately 60° to 90° C., and more preferably, at about 70° to about 80° C. This may be performed by placing the mold assembly holding the composite in a compressed state in a water bath or in a circulating convection oven where curing takes place over a period of hours.

The following specific examples demonstrate the methods and articles of the invention. However, it is to be understood that these examples are for illustrative purposes only and do not purport to be wholly definitive as to conditions and scope.

EXAMPLE I

In order to perform comparative studies and also demonstrate the bond strength of composite structures according to the invention, test denture base materials consisting of rigid acrylic resin (PMMA) rectangularly shaped having a dimension of 7.5 cm×2.5 cm×4 mm thickness were prepared. Prior to application of the coupling/bonding agent, the acrylic specimens were lightly abraded with a sandblaster or 240 grit abrasive paper, rinsed and stored in room temperature water. Before application of the coupling agent, the acrylic specimens were dried and cleaned with methanol. A 25 percent solution of a vinyltriacetoxysilane coupling agent in methylmethacrylate monomer was brushed onto one surface of each rectangular shaped rigid denture base specimen as a thin coating and allowed to air dry at room temperature for 5 minutes. A second coating of the coupling agent was applied over the first coating and dried for 30 minutes in an oven at 70° C.

Equal parts by weight of packages A and B of Dow-Corning's Silastic Q7-4720 Medical grade ETR silicone elastomer were thoroughly blended together manually on a plate. Individual silane coated acrylic sections were seated in gypsum molds with a separating medium previously applied and the blended elastomer packed against each section. Two or three trial packings were used with excess flash removed between each step. The mold assembly was then cured at 74° C. for 8 hours in a water bath. The test strips thus consisted of 4 mm thick rigid acrylic backing with a 3 mm thick lining layer bonded over 5 cm of specimen length. Bonded test pieces were stored at 37° C. for 30 days prior to testing.

Ends of the peel test specimens were secured in serrated grips with the soft lining tab bent back to give a peeling angle of 180°. The unit was placed on an Instron testing apparatus.

This machine uses interchangeable resistance strain gage cells which measure tensile or compressive loads. Load is applied with a constant strain rate by motion of the crosshead which carries the moving jaw. Stress-strain recordings are made on a chart which moves in synchronization with the crosshead.

Test specimens were subjected to a peeling force by separation of the grips at a crosshead speed of 30 cm/min. Force per unit width of the bond necessary to cause detachment of the elastomers was calculated as determined by ASTM D 903 and presented in Table I.

EXAMPLE II

In order to demonstrate the performance of vinyltris(methylethylketoximine)silane (V-5050) and vinyltriacetoxysilane (V-4800) as coupling agents for the silicone elastomer Silastic Q7-4720, specimen samples were prepared according to the protocol outlined in Example I. Samples were prepared using both undiluted coupling agent and dilution with methyl methacrylate monomer to provide 25% solutions. Control specimens were fabricated without silane coupling agent.

For comparison, peel strength determinations were also performed on a commercial soft liner material, Molloplast B, available through Buffalo Dental Supply Co., New York, N.Y. Molloplast B is a peroxide catalyzed, heat-cured silicone rubber. Analysis of the Molloplast B coupling agent, Primo, seems to show it is a vinyltriethoxy silane in methylmethacrylate monomer. Peel strength specimens were prepared as follows.

Test denture base materials consisting of rigid acrylic resin (PMMA) rectangularly shaped having a dimension of 7.5 cm×2.5 cm×4 mm thickness were prepared. Prior to application of the coupling/bonding agent, the acrylic specimens were lightly abraded with a sandblaster or 240 grit abrasive paper, rinsed and stored in room temperature water. Before application of the coupling agent, the acrylic specimens were dried and cleaned with methanol. The liquid bonding agent, Primo, was brushed onto one surface of each rectangular shaped rigid denture base specimen as a thin coating and allowed to air dry at room temperature for 90 minutes.

Individual coated acrylic sections were seated in gypsum molds and the one part Molloplast B silicone packed against each section. Three trial packings were used with excess flash removed between each step. The mold assembly was then cured at 74° C. for 8 hours in a water bath. The test strips thus consisted of 4 mm thick rigid acrylic backing with a 3 mm thick lining layer bonded over 5 cm of specimen length. Bonded test pieces were stored at 37° C. for 30 days prior to testing.

Ends of the peel test specimens were secured in serrated grips with the soft lining tab bent back to give a peeling angle of 180°. The unit was placed on an Instron testing apparatus. Test specimens were subjected to a peeling force by separation of the grips at a crosshead speed of 30 cm/min. The force per unit width of the bond necessary to cause detachment of the elastomer was calculated and presented in Table I.

TABLE I

| MATERIAL | BOND STRENGTH kN/m | |
|---|---|---|
| | MEAN | SD |
| Q7-4720 (100% V5050) | 10.50 | .81 |
| Q7-4720 (25% V5050) | 9.04 | 1.22 |
| Q7-4720 (100% V4800) | 10.59 | 1.91 |
| Q7-4720 (25% V4800) | 10.88 | 1.22 |
| Q7-4720 (CONTROL-NO SILANE) | 1.65 | .30 |
| MOLLOPLAST-B | .15 | .07 |

N = 10 PER MATERIAL

Bond strength testing indicates the tenacity of the bond between the elastomer-acrylic composite. This test provides an indication of the clinical success of a resilient liner.

The data (Table I) shows that the bond strength of Silastic Q7-4720 test specimens with coatings of silane coupling agent is approximately ten times greater than those Q7-4720 specimens with no silane (control). Also, Q7-4720/silane coated specimens failed with a thin layer of the elastomer attached to the acrylic substrate (cohesive failure) rather than by peeling of the bond between the elastomer and acrylic in the control specimens (adhesive failure). In comparison with Q7-4720 test specimens coated with 100% silane, those coated with a 25% solution of silane in methylmethacrylate monomer showed substantially no deterioration in bond strength.

Molloplast-B test specimens demonstrated a bond that exceeded the strength of the material, i.e. the elastomer portion of the specimen ruptured before a consistent peel was observed at relatively low force levels.

EXAMPLE III

An impression of the patient's existing upper or lower edentulous jaw is taken with the denture to be relined using conventional techniques. The unit is invested in a dental flask forming a stone model. Such methods are generally known by persons of ordinary skill. After the gypsum stone has hardened sufficiently, the flask is gently separated. Immersion in hot (50° C.-60° C.) water for approximately 5 minutes may facilitate separation. The impression material is removed and the denture base is prepared to provide sufficient space for the resilient liner, optimally 2 to 3 mm in all areas. A tin foil substitute separating medium is applied to all gypsum surfaces.

The acrylic surface which will contact the resilient liner is cleaned with methanol. A 25% solution of vinyltriacetoxysilane coupling agent in methylmethacrylate monomer is brushed onto the cleaned acrylic surface as a thin coat and allowed to dry 5 minutes at room temperature. A second coat is applied and dried 30 minutes in an oven at 65° C.-70° C. A blended mix of equal parts by weight of Silastic Q7-4720, A and B, is formed into a roll and placed onto the coated acrylic denture base. Trial packing twice with a thin plastic separating sheet will produce an even distribution of material. The plastic sheet is removed prior to closing the flask for processing. The mold assembly holding the coated/lined prosthetic appliance in a compressed state is then placed in a water bath or circulating convection oven for 8 hours at 74° C. The assembly is then cooled and the appliance removed from the flask. The cured/bonded resilient liner is then trimmed and finished by standard techniques.

EXAMPLE IV

Obturators may be used to seal defects in the head and face caused by congenital clefts or surgical procedures. Although surgical repair may be the treatment of choice, treatment with a prosthesis is often indicated. Former methods necessitated mechanical retention of the resilient obturator portion onto the rigid acrylic.

The construction of an obturator to seal a defect in the hard palate of the upper jaw is described. The obturator bulb portion may be hollow or solid. The jaw may be edentulous, partially endentulous or having a full complement of teeth. An impression of the upper jaw is taken using standard techniques. A positive stone model is made from the impression. After the gypsum stone has hardened sufficiently, the impression is gently separated. Immersion in hot (50° C.-60° C.) water for approximately 5 minutes may facilitate the separation. The model is then invested in a conventional dental flask. Such methods are generally known by persons of ordinary skill. The defect is blocked out with wax or other suitable medium and a plate processed in acrylic PMMA resin with or without prosthetic teeth using standard techniques. The cured PMMA section is then separated from the stone model and the blockout medium is removed from the defect.

The margins of the obturator may line the entire palatal surface and terminate at the periphery of the acrylic. Alternatively, the obturator margins may terminate at any portion within the outer border of the acrylic. The acrylic surface which will contact the lining/obturator is cleaned with methanol. A 25% solution of vinyltriacetoxysilane coupling agent in methylmetacrylate monomer is brushed onto the cleaned acrylic surface as a thin coat and allowed to dry 5 minutes at room temperature. A second coat is applied and dried 30 minutes in an oven at 65° C.-70° C.

A blended mix of equal parts by weight of Silastic Q7-4720, A and B, is formed and placed into the defect and extended to the desired palatal coverage. Severe undercuts within the defect may be blocked out with wax or other suitable medium. Trial packing twice with a plastic sheet between the rigid acrylic and Silastic Q7-4720 will produce an even distribution of material. The plastic sheet is removed prior to closing the flask for processing. The mold assembly holding the prosthetic appliance in a compressed state is then placed in a water bath or circulating convection oven for 8 hours at 74° C. The assembly is then cooled and the appliance removed from the flask. The cured/bonded resilient obturator/liner is then trimmed and finished using standard techniques.

While the invention has been described in conjunction with specific examples thereof, this is illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

What is claimed is:

1. A method of forming a composite-like structure of a silicone elastomer and a prosthetic appliance which comprises, in the order indicated, the steps of:
   a) applying a film of silane coupling agent to said appliance, said coupling agent comprising a compound of the formula:

$$X-Si-(R)_3$$

wherein X is methyl or vinyl and R is $-O-CO-CH_3$ or $-O-N=C-(CH_3)-CH_2CH_3$;
   b) drying the silane film on said appliance;
   c) applying to said dried silane film on said appliance a silicone elastomer to form said composite-like structure, said elastomer consisting essentially of a platinum-catalyzed organopolysiloxane copolymer of from about 99.90 to about 99.99 mole percent dimethyl siloxane units and from about 0.01 to about 0.10 mole percent methylvinyl siloxane units; and
   d) curing the composite-like structure at above ambient temperature conditions.

2. The method of claim 1 which said copolymer preferably consists essentially of from 99.5 to 99.7 mole percent dimethyl siloxane units and from 0.03 to 0.05 mole percent methylvinyl siloxane units.

3. The method of claim 1 wherein the coupling agent comprises a compound selected from the group consisting of methyltriacetoxysilane, vinyltriacetoxysilane, methyltris(methylethylketoximine)silane and vinyltris(methylethylketoximine)silane.

4. The method of claim 1 wherein the coupling agent is vinyltriacetoxysilane.

5. The method of claim 1 wherein the prosthetic appliance is an article selected from the group consisting of a prosthodontic appliance and a maxillofacial prosthetic device.

6. The method of claim 1 wherein the appliance is an article selected from the group consisting of a denture, interim prosthesis, transitional prosthesis, a splint, speech aid device and an obturator.

7. The method of claim 1 wherein the appliance is fabricated at least in part from a cured denture base polymer.

8. The method of claim 7 wherein the cured denture base polymer is an acrylic.

9. The method of claim 7 wherein the denture base polymer is a material selected from the group consisting of poly(methylmethacrylate), a copolyester and a polyurethane.

10. The method of claim 7 wherein the denture base polymer comprises a light curable urethane dimethacrylate polymer.

11. The method of claim 1 wherein drying said silane coated appliance according to step (b) is performed at above ambient temperature conditions.

12. The method of claim 1 which said silicone elastomer is further characterized as having a specific gravity ranging from about 1.08 to 1.12 as determined by ASTM D 792; a Shore A durometer in a range from about 19 to about 27 as determined by ASTM D 2240; a tear strength of at least 140 ppi as determined by ASTM D 624, Die B; a tensile strength of at least 1100 psi as determined by ASTM D 412, Die C; and an elongation of at least 1050 percent as determined by ASTM D 412, after having been press-cured for about 10 minutes at about 230° to about 250° F. and equilibrated for about 14 to about 18 hours at about 21° to about 25° C.

* * * * *

UNITED STATES PATENT AND TRADEMARK OFFICE
CERTIFICATE OF CORRECTION

PATENT NO. : 5,112,640
DATED : May 12, 1992
INVENTOR(S) : Stephen P. Warunek, et al.

It is certified that error appears in the above-indentified patent and that said Letters Patent is hereby corrected as shown below:

Column 9, claim 2, line 45, change "99.5 to 99.7" to --99.95 to 99.97--.

Signed and Sealed this

Fifteenth Day of March, 1994

BRUCE LEHMAN

Attest:

Attesting Officer

Commissioner of Patents and Trademarks